(12) United States Patent
Coates et al.

(10) Patent No.: US 11,951,119 B2
(45) Date of Patent: Apr. 9, 2024

(54) COMBINATION COMPRISING ZIDOVUDINE AND AN ANTIMICROBIAL COMPOUND

(71) Applicant: Helperby Therapeutics Limited, London (GB)

(72) Inventors: Anthony Coates, London (GB); Yanmin Hu, London (GB)

(73) Assignee: Helperby Therapeutics Limited, London (GB)

( * ) Notice: Subject to any disclaimer, the term of this patent is extended or adjusted under 35 U.S.C. 154(b) by 695 days.

(21) Appl. No.: 17/051,549

(22) PCT Filed: Apr. 12, 2019

(86) PCT No.: PCT/GB2019/051062
§ 371 (c)(1),
(2) Date: Oct. 29, 2020

(87) PCT Pub. No.: WO2019/211576
PCT Pub. Date: Nov. 7, 2019

(65) Prior Publication Data
US 2022/0117991 A1  Apr. 21, 2022

(30) Foreign Application Priority Data
Apr. 30, 2018  (GB) ..................... 1807046

(51) Int. Cl.
| A61K 31/7072 | (2006.01) |
| A61K 31/4178 | (2006.01) |
| A61K 31/431 | (2006.01) |
| A61K 31/545 | (2006.01) |
| A61K 31/55 | (2006.01) |
| A61K 31/665 | (2006.01) |
| A61P 31/04 | (2006.01) |

(52) U.S. Cl.
CPC ...... *A61K 31/7072* (2013.01); *A61K 31/4178* (2013.01); *A61K 31/431* (2013.01); *A61K 31/545* (2013.01); *A61K 31/55* (2013.01); *A61K 31/665* (2013.01); *A61P 31/04* (2018.01)

(58) Field of Classification Search
CPC .... A61K 31/55; A61K 31/431; A61K 31/655; A61K 31/4178; A61K 31/7072; A61K 2300/00; A61P 31/00; A61P 31/04
USPC .......................................................... 514/50
See application file for complete search history.

(56) References Cited

FOREIGN PATENT DOCUMENTS

| JP | 2004534792 A | 11/2004 |
| WO | 0028074 | 5/2000 |
| WO | 02100402 A1 | 12/2002 |
| WO | 2005014585 A1 | 2/2005 |
| WO | WO 2006/021965 A1 * | 3/2006 ............. A61K 45/06 |
| WO | 2014147405 A1 | 9/2014 |
| WO | 2015114340 A1 | 8/2015 |
| WO | 2017098274 A1 | 6/2017 |
| WO | 2018011562 A1 | 1/2018 |

OTHER PUBLICATIONS

Schwartzman et al, The American Journal of Medicine, 1991, 50, 595-600.*
Elwell et al, Antimicrobial Agents and Chemotherapy, 1987, 31(2), 274-280.*
Tasbakan et al, International Journal of Antibacterial Agents, 2012, 40, 554-556.*
Graninger, International Journal of Antibacterial Agents, 2003, 22, S73-S78.*
Neuner et al, Antimicrobial Agents and Chemotherapy, 2012, 56(11), 5744-5746.*
Piddock et al, Journal of Antimicrobial Chemotherapy, 2003, 52, 500-502.*
Study for Combined Effects of Antimicrobial Agents Against Multidrug-Resistant Pseudomonas aeruginosa Detected in Our Hospital, Medical Test (The Japanese Journal of Medical Technology), vol. 57, No. 4, 2008, p. 377.
Japanese Office Action, Notification of Reason for Rejection, Application No. 2020-560822, dated Jan. 27, 2023.
Herrmann et al., "Intracellular Activity of Zidovudine (3'-Azido-3'-Deoxythymidine, AZT) against *Salmonella typhimurium* in the Macrophage Cell Line J774-2", Antimicrobial Agents and Chemotherapy, American Society for Microbiology, 1992, vol. 36, No. 5, pp. 1081-1085.
Coates et al., "The Future Challenges Facing the Development of New Antimicrobial Drugs", Nature Reviews, Drug Discovery, 2002, vol. 1, issue 11, pp. 895-910.
Orhan et al., Synergy Tests by E Test and Checkerboard Methods of Antimicrobial Combinations against *Brucella melitensis*, Journal of Clinical Microbiology, 2005, vol. 43, No. 1, pp. 140-143.
Lippincott et al., "Remington: The Science and Practice of Pharmacy", A Wolters Kluwer Company, 2005, 21st Edition.
Doléans-Jordheim et al., "Zidovudine (AZT) has a bactericidal effect on enterobacteria and induces genetic modifications in resistant strains" Eur J Clin Microbiol Infect Dis, 2011, vol. 30, pp. 1249-1256.
Hu et al., "Enhancement by novel anti-methicillin-resistant *Staphylococcus aureus* compound HT61 of the activity of neomycin, gentamicin, mupirocin and chlorhexidine: in vitro and in vivo studies", Journal of Antimicrobial Chemotherapy, 2013, vol. 68, pp. 374-384.

(Continued)

*Primary Examiner* — Ganapathy Krishnan
(74) *Attorney, Agent, or Firm* — MacMillan, Sobanski & Todd, LLC

(57) ABSTRACT

The invention provides a combination comprising zidovudine or a pharmaceutically acceptable derivative thereof and an antimicrobial compound selected from nitrofurantoin, mecillinam, fosfomycin, cephalexin and faropenem, or a pharmaceutically acceptable derivative or prodrug thereof. These combinations are particularly useful for the treatment of microbial infections.

16 Claims, 5 Drawing Sheets

(56) References Cited

OTHER PUBLICATIONS

World Health Organization, "Antimicrobial Resistance Global Report on Surveillance", World Health Organization, 2014.
Public Health England, English surveillance programme for antimicrobial utilisation and resistance (ESPAUR), 2017.
PCT International Search Report and Written Opinion, Application No. PCT/GB2019/051062, dated Jul. 16, 2019.
Schwartzman, et al., "Staphylococcal Pyomyositis in Patients Infected by the Human Immunodeficiency Virus", The American Journal of Medicine, 1991, vol. 90, No. 1, pp. 595-600.

* cited by examiner

Nitrofurantoin

| | 16 | 8 | 4 | 2 | 1 | 0.5 | 0.25 | 0.125 | 0.063 | 0.031 | 0.016 | 0 |
|---|---|---|---|---|---|---|---|---|---|---|---|---|
| 2 | 0.04 | 0.04 | 0.04 | 0.38 | 0.05 | 0.05 | 0.07 | 0.13 | 0.06 | 0.09 | 0.52 | 0.08 |
| 1 | 0.04 | 0.04 | 0.04 | 0.06 | 0.06 | 0.06 | 0.07 | 0.06 | 0.07 | 0.07 | 0.07 | 0.46 |
| 0.5 | 0.04 | 0.04 | 0.06 | 0.06 | 0.07 | 0.39 | 0.17 | 0.07 | 0.07 | 0.07 | 0.11 | 0.28 |
| 0.25 | 0.04 | 0.04 | 0.06 | 0.07 | 0.07 | 0.08 | 0.08 | 0.08 | 0.09 | 0.09 | 0.11 | 0.15 |
| 0.125 | 0.04 | 0.04 | 0.08 | 0.09 | 0.09 | 0.25 | 0.10 | 0.10 | 0.11 | 0.11 | 0.12 | 0.35 |
| 0.063 | 0.04 | 0.06 | 0.09 | 0.23 | 0.14 | 0.21 | 0.15 | 0.16 | 0.16 | 0.20 | 0.18 | 0.21 |
| 0.031 | 0.04 | 0.15 | 0.16 | 0.21 | 0.27 | 0.29 | 0.32 | 0.30 | 0.31 | 0.32 | 0.30 | 0.37 |
| 0 | 0.04 | 0.65 | 0.82 | 0.82 | 0.86 | 0.94 | 0.87 | 0.95 | 0.97 | 0.94 | 0.99 | 0.94 |
| FIC index | | 0.31 | 0.25 | 0.19 | 0.16 | 0.14 | 0.13 | 0.25 | 0.25 | 0.50 | | |

AZT (row labels on left)

Fig. 1

|     | Faropenem | | | | | | | | | | | |
| --- | --- | --- | --- | --- | --- | --- | --- | --- | --- | --- | --- | --- |
|     | 2 | 1 | 0.5 | 0.25 | 0.125 | 0.063 | 0.031 | 0.016 | 0.008 | 0.004 | 0.002 | 0 |
| 2   | 0.05 | 0.05 | 0.05 | 0.05 | 0.07 | 0.10 | 0.09 | 0.05 | 0.07 | 0.41 | 0.17 | 0.08 |
| 1   | 0.06 | 0.05 | 0.05 | 0.05 | 0.06 | 0.07 | 0.06 | 0.07 | 0.07 | 0.09 | 0.07 | 0.09 |
| 0.5 | 0.06 | 0.05 | 0.05 | 0.05 | 0.08 | 0.06 | 0.08 | 0.09 | 0.09 | 0.08 | 0.08 | 0.50 |
| 0.25 | 0.06 | 0.05 | 0.05 | 0.05 | 0.06 | 0.07 | 0.09 | 0.09 | 0.09 | 0.10 | 0.09 | 0.18 |
| 0.125 | 0.06 | 0.05 | 0.05 | 0.06 | 0.08 | 0.09 | 0.12 | 0.15 | 0.11 | 0.12 | 0.11 | 0.16 |
| 0.063 | 0.06 | 0.06 | 0.06 | 0.06 | 0.09 | 0.12 | 0.13 | 0.16 | 0.19 | 0.18 | 0.17 | 0.37 |
| 0.031 | 0.07 | 0.05 | 0.06 | 0.07 | 0.11 | 0.17 | 0.22 | 0.27 | 0.26 | 0.25 | 0.27 | 0.38 |
| 0   | 0.07 | 0.08 | 0.10 | 0.35 | 0.58 | 0.79 | 0.86 | 0.93 | 0.97 | 0.96 | 0.97 | 0.91 |
| FIC index | | | 0.28 | 0.16 | 0.13 | 0.16 | 0.27 | | 0.50 | | | |

(AZT rows on left axis)

Fig. 2

Mecillinam

| | 1 | 0.5 | 0.25 | 0.125 | 0.063 | 0.031 | 0.016 | 0.008 | 0.004 | 0.002 | 1E-03 | 0 |
|---|---|---|---|---|---|---|---|---|---|---|---|---|
| 2 | 0.06 | 0.06 | 0.06 | 0.06 | 0.06 | 0.04 | 0.06 | 0.14 | 0.07 | 0.06 | 0.06 | 0.06 |
| 1 | 0.05 | 0.04 | 0.04 | 0.04 | 0.04 | 0.04 | 0.07 | 0.09 | 0.10 | 0.07 | 0.08 | 0.08 |
| 0.5 | 0.06 | 0.04 | 0.04 | 0.04 | 0.04 | 0.05 | 0.06 | 0.07 | 0.07 | 0.08 | 0.09 | 0.12 |
| 0.25 | 0.06 | 0.04 | 0.04 | 0.05 | 0.04 | 0.05 | 0.06 | 0.08 | 0.09 | 0.23 | 0.11 | 0.15 |
| 0.125 | 0.06 | 0.04 | 0.05 | 0.05 | 0.05 | 0.06 | 0.07 | 0.09 | 0.12 | 0.17 | 0.13 | 0.19 |
| 0.063 | 0.06 | 0.05 | 0.04 | 0.04 | 0.05 | 0.06 | 0.09 | 0.11 | 0.15 | 0.14 | 0.20 | 0.36 |
| 0.031 | 0.06 | 0.05 | 0.05 | 0.05 | 0.06 | 0.08 | 0.15 | 0.21 | 0.33 | 0.26 | 0.27 | 0.43 |
| 0 | 0.09 | 0.09 | 0.09 | 0.09 | 0.27 | 0.44 | 0.56 | 0.64 | 0.70 | 0.73 | 0.72 | 0.79 |
| FIC index | | 0.28 | 0.16 | 0.09 | 0.28 | 0.25 | 0.31 | | | | | |

AZT (row labels)

Fig. 3

Cephalexin

| AZT \ | 16 | 8 | 4 | 2 | 1 | 0.5 | 0.25 | 0.125 | 0.063 | 0.031 | 0.016 | 0 |
|---|---|---|---|---|---|---|---|---|---|---|---|---|
| 2 | 0.04 | 0.04 | 0.04 | 0.04 | 0.46 | 0.04 | 0.04 | 0.04 | 0.35 | 0.04 | 0.34 | 0.05 |
| 1 | 0.04 | 0.04 | 0.04 | 0.04 | 0.04 | 0.04 | 0.04 | 0.04 | 0.04 | 0.04 | 0.04 | 0.04 |
| 0.5 | 0.04 | 0.04 | 0.05 | 0.04 | 0.04 | 0.04 | 0.39 | 0.04 | 0.50 | 0.05 | 0.05 | 0.47 |
| 0.25 | 0.04 | 0.04 | 0.05 | 0.05 | 0.05 | 0.05 | 0.05 | 0.50 | 0.16 | 0.05 | 0.05 | 0.30 |
| 0.125 | 0.04 | 0.04 | 0.06 | 0.07 | 0.37 | 0.39 | 0.06 | 0.06 | 0.06 | 0.06 | 0.06 | 0.07 |
| 0.0625 | 0.04 | 0.04 | 0.08 | 0.21 | 0.09 | 0.09 | 0.21 | 0.09 | 0.18 | 0.09 | 0.17 | 0.08 |
| 0.0313 | 0.04 | 0.04 | 0.09 | 0.23 | 0.26 | 0.20 | 0.23 | 0.20 | 0.24 | 0.23 | 0.24 | 0.26 |
| 0 | 0.04 | 0.04 | 0.39 | 0.77 | 1.06 | 1.08 | 1.06 | 1.08 | 1.10 | 1.10 | 1.08 | 0.97 |
| FIC index | | | | 0.38 | 0.38 | 0.31 | 0.28 | | | | | |

Fig. 4

Fosfomycin

| | | 8 | 4 | 2 | 1 | 0.5 | 0.25 | 0.125 | 0.063 | 0.031 | 0.016 | 0.008 | 0 |
|---|---|---|---|---|---|---|---|---|---|---|---|---|---|
| AZT | 2 | 0.04 | 0.04 | 0.04 | 0.04 | 0.38 | 0.04 | 0.18 | 0.04 | 0.04 | 0.04 | 0.04 | 0.05 |
| | 1 | 0.04 | 0.04 | 0.04 | 0.31 | 0.38 | 0.04 | 0.05 | 0.04 | 0.04 | 0.04 | 0.04 | 0.04 |
| | 0.5 | 0.04 | 0.04 | 0.04 | 0.04 | 0.04 | 0.10 | 0.19 | 0.04 | 0.04 | 0.04 | 0.05 | 0.05 |
| | 0.25 | 0.04 | 0.13 | 0.05 | 0.05 | 0.27 | 0.43 | 0.35 | 0.05 | 0.05 | 0.27 | 0.05 | 0.14 |
| | 0.125 | 0.06 | 0.07 | 0.07 | 0.07 | 0.27 | 0.15 | 0.07 | 0.26 | 0.18 | 0.33 | 0.08 | 0.19 |
| | 0.0625 | 0.07 | 0.07 | 0.08 | 0.08 | 0.09 | 0.32 | 0.11 | 0.09 | 0.10 | 0.17 | 0.22 | 0.28 |
| | 0.0313 | 0.07 | 0.08 | 0.09 | 0.10 | 0.11 | 0.14 | 0.18 | 0.19 | 0.19 | 0.21 | 0.19 | 0.21 |
| | 0 | 0.19 | 0.29 | 0.37 | 0.47 | 0.61 | 0.74 | 0.83 | 0.94 | 0.95 | 0.97 | 0.87 | 0.96 |
| FIC index | | | | 0.38 | 0.25 | | | | | | | | |

Fig. 5

COMBINATION COMPRISING ZIDOVUDINE AND AN ANTIMICROBIAL COMPOUND

CROSS-REFERENCED RELATED APPLICATIONS

This application is a national stage application of international application PCT/GB2019/051062, filed under the authority of the Patent Cooperation Treaty on Apr. 12, 2019, published; which claims priority to United Kingdom Application No. 1807046.6, filed on Apr. 30, 2018. The entire disclosure of each of the aforementioned applications is hereby incorporated herein by reference for all purposes.

FIELD OF THE INVENTION

The present invention relates to the combination of zidovudine or a pharmaceutically acceptable derivative thereof with an antibiotic compound or a pharmaceutically acceptable derivative or prodrug thereof selected from the group defined herein. The present invention also relates to the use of these combinations for the treatment of microbial infections. In particular, it relates to the use of such combinations to kill multiplying (i.e. log phase) microorganisms associated with microbial infections, e.g. Gram-negative bacterial infections including urinary tract infections.

BACKGROUND

Before the introduction of antibiotics, patients suffering from acute microbial infections (e.g. tuberculosis or *pneumonia*) had a low chance of survival. For example, mortality from tuberculosis was around 50%. Although the introduction of antimicrobial agents in the 1940s and 1950s rapidly changed this picture, bacteria have responded by progressively gaining resistance to commonly used antibiotics. Now, every country in the world has antibiotic-resistant bacteria.

Indeed, more than 70% of bacteria that give rise to hospital acquired infections in the USA resist at least one of the main antimicrobial agents that are typically used to fight infection (Nature Reviews, Drug Discovery, 1, 895-910 (2002)). The World Health Organization has therefore classified antimicrobial resistance as a "serious threat [that] is no longer a prediction for the future, it is happening right now in every region of the world and has the potential to affect anyone, of any age, in any country" ("Antimicrobial resistance: global report on surveillance", The World Health Organization, April 2014).

One group of antibiotics which is facing critical resistance problems is the compounds used to treat urinary tract infections or UTIs. In a recent report from Public Health England, it was noted that antimicrobial resistance was common in more than 1 million urinary tract infections (UTIs) caused by bacteria identified in NHS laboratories in 2016 («English Surveillance Programme for Antimicrobial Utilisation and Resistance (ESPAUR)»(2017)).

A solution to the growing problem of resistant bacteria causing urinary tract infections is therefore desperately needed.

In most cases UTIs are treated with a short course of antibiotics taken by mouth such as trimethoprim, nitrofurantoin or fosfomycin. Cephalexin may also be used as well as mecillinam or its orally active prodrug pivmecillinam, faropenem and nitroxoline (5-nitro-8-hydroxyquinoline).

Surprisingly and of huge importance to the fight against antimicrobial resistance in the treatment of urinary tract infections, the Applicant has discovered that the antiretroviral drug zidovudine has a synergistic effect with certain urinary tract antibiotics, namely nitrofurantoin, mecillinam, fosfomycin, cephalexin and faropenem. In other words, the combination(s) has a greater biological activity than the expected additive effect of each agent at the stated dosage level.

Zidovudine (AZT) is a nucleoside analogue reverse-transcriptase inhibitor, a type of antiretroviral drug which is used for the treatment of HIV/AIDS infection. As well as its antiretroviral activity, the antibacterial effect of zidovudine (AZT) has been demonstrated both in vitro and in vivo with experimental models of gram-negative bacteria infections (Hermann et al., Antimicrob Agents Chemther. 1992 May; 36(5): 1081-1085). There have also been reports of zidovudine being active as an anti-microbial when combined with the antibiotic gentamicin (Doleans-Jordheim A. et al., Eur J Clin Microbiol Infect Dis. 2011 October; 30(10):1249-56).

WO2014/147405 describes the use of zidovudine in combination with a polymyxin selected from colistin and polymyxin B for treating a microbial infection. WO2015/114340 describes the use of zidovudine in combination with a polymyxin selected from colistin or polymyxin B, an anti-tuberculosis antibiotic selected from rifampicin, rifapentine or rifabutin and optionally piperine, for treating a microbial infection. WO2018/011562 describes a combination comprising zidovudine and a carbapenem, optionally with a polymyxin selected from polymyxin B and polymyxin E.

Synergy is not, however, predictable or expected when two actives are used in combination. The present invention is therefore based on the unexpected finding that zidovudine or a pharmaceutically acceptable derivative thereof exhibits synergistic antimicrobial activity when used in combination with a compound selected from nitrofurantoin, mecillinam and faropenem, or a pharmaceutically acceptable derivative or prodrug thereof, against log phase (i.e. multiplying) microorganisms. Notably synergy is seen when the combinations are used against gram-negative bacteria.

The surprising biological activity of the combinations of the present invention offers the opportunity to rejuvenate certain urinary tract antibiotics, against which bacterial resistance has developed.

Synergy in the context of antimicrobial drugs is measured in a number of ways that conform to the generally accepted opinion that "synergy is an effect greater than additive". One of the ways to assess whether synergy has been observed is to use the "chequerboard" technique. This is a well-accepted method that leads to the generation of a value called the fractional inhibitory concentration index (FICI). Orhan et al., J. Clin. Microbiol. 2005, 43(1):140 describes the chequerboard method and analysis in the paragraph bridging pages 140-141, and explains that the FICI value is a ratio of the sum of the MIC (Minimum Inhibitory Concentration) level of each individual component alone and in the mixture. The combination is considered synergistic when the $\Sigma$FIC is ≤0.5, indifferent when the $\Sigma$FIC is >0.5 but <4.0, and antagonistic when the $\Sigma$FIC is >4.0.

Another accepted test for ascertaining the presence or absence of synergy is to use time-kill methods. This involves the dynamic effect of a drug combination being compared to each drug alone when assessing the effect on bacterial log or stationary-growth over time. Again, the possible results are for synergistic, additive or antagonistic effects.

SUMMARY OF THE INVENTION

In one aspect the present invention provides a combination of zidovudine or a pharmaceutically acceptable derivative thereof and an antimicrobial compound selected from nitrofurantoin, mecillinam, fosfomycin, cephalexin and faropenem or a pharmaceutically acceptable derivative or prodrug thereof.

In one embodiment the combination is of zidovudine or a pharmaceutically acceptable derivative thereof and nitrofurantoin or a pharmaceutically acceptable derivative or prodrug thereof.

In another embodiment the combination is of zidovudine or a pharmaceutically acceptable derivative thereof and mecillinam or a pharmaceutically acceptable derivative or prodrug thereof, e.g. pivmecillinam or a pharmaceutically acceptable derivative thereof such as pivmecillinam hydrochloride.

In another embodiment the combination is of zidovudine or a pharmaceutically acceptable derivative thereof and fosfomycin or a pharmaceutically acceptable derivative or prodrug thereof, e.g. fosfomycin calcium, fosfomycin sodium, fosfomycin trometamol or fosfomycin tromethamine.

In another embodiment the combination is of zidovudine or a pharmaceutically acceptable derivative thereof and cephalexin or a pharmaceutically acceptable derivative or prodrug thereof (e.g. cephalexin hydrate, cephalexin monohydrate or cephalexin phthalidyl ester).

In another embodiment the combination is of zidovudine or a pharmaceutically acceptable derivative thereof and faropenem or a pharmaceutically acceptable derivative or prodrug thereof, e.g. faropenem sodium, faropenem sodium hydrate or faropenem medoxomil.

In another aspect the present invention provides the use of zidovudine or a pharmaceutically acceptable derivative thereof in combination with an antimicrobial compound selected from nitrofurantoin, mecillinam, fosfomycin, cephalexin and faropenem or a pharmaceutically acceptable derivative or prodrug thereof, in the manufacture of a medicament for treating a microbial infection.

In one embodiment the use is of zidovudine or a pharmaceutically acceptable derivative thereof in combination with nitrofurantoin or a pharmaceutically acceptable derivative or prodrug thereof in the manufacture of a medicament for treating a microbial infection.

In another embodiment the use is of zidovudine or a pharmaceutically acceptable derivative thereof in combination with mecillinam or a pharmaceutically acceptable derivative or prodrug thereof (e.g. pivmecillinam or a pharmaceutically acceptable derivative thereof such as pivmecillinam hydrochloride) in the manufacture of a medicament for treating a microbial infection.

In another embodiment the use is of zidovudine or a pharmaceutically acceptable derivative thereof in combination with fosfomycin or a pharmaceutically acceptable derivative or prodrug thereof, (e.g. fosfomycin calcium, fosfomycin sodium, fosfomycin trometamol or fosfomycin tromethamine) in the manufacture of a medicament for treating a microbial infection.

In another embodiment the use is of zidovudine or a pharmaceutically acceptable derivative thereof in combination with cephalexin or a pharmaceutically acceptable derivative or prodrug thereof (e.g. cephalexin hydrate, cephalexin monohydrate or cephalexin phthalidyl ester) in the manufacture of a medicament for treating a microbial infection.

In another embodiment the use is of zidovudine or a pharmaceutically acceptable derivative thereof in combination with faropenem or a pharmaceutically acceptable derivative or prodrug thereof (e.g. e.g. faropenem sodium, faropenem sodium hydrate or faropenem medoxomil) in the manufacture of a medicament for treating a microbial infection.

In another aspect the present invention provides the use of an antimicrobial compound selected from nitrofurantoin, mecillinam, fosfomycin, cephalexin and faropenem or a pharmaceutically acceptable derivative or prodrug thereof, in combination with zidovudine or a pharmaceutically acceptable derivative thereof, in the manufacture of a medicament for treating a microbial infection.

In one embodiment the use is of nitrofurantoin or a pharmaceutically acceptable derivative thereof in combination with zidovudine or a pharmaceutically acceptable derivative or prodrug thereof, in the manufacture of a medicament for treating a microbial infection.

In another embodiment the use is of mecillinam or a pharmaceutically acceptable derivative or prodrug thereof (e.g. pivmecillinam or a pharmaceutically acceptable derivative thereof such as pivmecillinam hydrochloride) in combination with zidovudine or a pharmaceutically acceptable derivative thereof in the manufacture of a medicament for treating a microbial infection.

In another embodiment the use is of fosfomycin or a pharmaceutically acceptable derivative or prodrug thereof (e.g. fosfomycin calcium, fosfomycin sodium, fosfomycin trometamol or fosfomycin tromethamine) in combination with zidovudine or a pharmaceutically acceptable derivative thereof in the manufacture of a medicament for treating a microbial infection.

In another embodiment the use is of cephalexin or a pharmaceutically acceptable derivative or prodrug thereof (e.g. cephalexin hydrate, cephalexin monohydrate or cephalexin phthalidyl ester) in combination with zidovudine or a pharmaceutically acceptable derivative thereof in the manufacture of a medicament for treating a microbial infection.

In another embodiment the use is of faropenem or a pharmaceutically acceptable derivative or prodrug thereof (e.g. faropenem sodium, faropenem sodium hydrate or faropenem medoxomil) in combination with zidovudine or a pharmaceutically acceptable derivative thereof in the manufacture of a medicament for treating a microbial infection.

Additionally the present invention provides in a further aspect the combination of zidovudine or a pharmaceutically acceptable derivative thereof and an antimicrobial compound selected from nitrofurantoin, mecillinam, fosfomycin, cephalexin and faropenem or a pharmaceutically acceptable derivative or prodrug thereof, for use in the treatment of a microbial infection, preferably for use in the treatment of a bacterial infection.

In one embodiment the combination for use in the treatment of a microbial infection is of zidovudine or a pharmaceutically acceptable derivative thereof and nitrofurantoin or a pharmaceutically acceptable derivative or prodrug thereof.

In another embodiment the combination for use in the treatment of a microbial infection is of zidovudine or a pharmaceutically acceptable derivative thereof and mecillinam or a pharmaceutically acceptable derivative or prodrug thereof (e.g. pivmecillinam, or a pharmaceutically acceptable derivative thereof such as pivmecillinam hydrochloride).

In another embodiment the combination for use in the treatment of a microbial infection is of zidovudine or a pharmaceutically acceptable derivative thereof and fosfomycin or a pharmaceutically acceptable derivative or prodrug thereof (e.g. fosfomycin calcium, fosfomycin sodium, fosfomycin trometamol or fosfomycin tromethamine).

In another embodiment the combination for use in the treatment of a microbial infection is of zidovudine or a pharmaceutically acceptable derivative thereof and cephalexin or a pharmaceutically acceptable derivative or prodrug thereof (e.g. cephalexin hydrate, cephalexin monohydrate or cephalexin phthalidyl ester).

In another embodiment the combination for use in the treatment of a microbial infection is of zidovudine or a pharmaceutically acceptable derivative thereof and faropenem or a pharmaceutically acceptable derivative or prodrug thereof (e.g. faropenem sodium, faropenem sodium hydrate or faropenem medoxomil).

In a further aspect, the invention provides a method of treating a microbial infection which comprises administering to a mammal, including man, zidovudine or a pharmaceutically acceptable derivative thereof in combination with an antimicrobial compound selected from nitrofurantoin, mecillinam, fosfomycin, cephalexin and faropenem or a pharmaceutically acceptable derivative or prodrug thereof.

There is also provided a pharmaceutical composition comprising zidovudine or a pharmaceutically acceptable derivative thereof in combination with an antimicrobial compound selected from nitrofurantoin, mecillinam, fosfomycin, cephalexin and faropenem or a pharmaceutically acceptable derivative or prodrug thereof, and a pharmaceutically acceptable adjuvant, diluent or carrier. In one embodiment the pharmaceutical composition is for use in the treatment of a microbial infection, preferably wherein the microbial infection is a bacterial infection, e.g. a gram-negative bacterial infection.

In one embodiment the pharmaceutical composition comprises zidovudine or a pharmaceutically acceptable derivative thereof in combination with nitrofurantoin or a pharmaceutically acceptable derivative or prodrug thereof, and a pharmaceutically acceptable adjuvant, diluent or carrier.

In another embodiment the pharmaceutical composition comprises zidovudine or a pharmaceutically acceptable derivative thereof in combination with mecillinam or a pharmaceutically acceptable derivative or prodrug thereof (e.g. pivmecillinam, or a pharmaceutically acceptable derivative thereof such as pivmecillinam hydrochloride), and a pharmaceutically acceptable adjuvant, diluent or carrier.

In another embodiment the pharmaceutical composition comprises zidovudine or a pharmaceutically acceptable derivative thereof in combination with fosfomycin or a pharmaceutically acceptable derivative or prodrug thereof (e.g. fosfomycin calcium, fosfomycin sodium, fosfomycin trometamol or fosfomycin tromethamine), and a pharmaceutically acceptable adjuvant, diluent or carrier.

In another embodiment the pharmaceutical composition comprises zidovudine or a pharmaceutically acceptable derivative thereof in combination with cephalexin or a pharmaceutically acceptable derivative or prodrug thereof (e.g. cephalexin hydrate, cephalexin monohydrate or cephalexin phthalidyl ester), and a pharmaceutically acceptable adjuvant, diluent or carrier.

In another embodiment the pharmaceutical composition comprises zidovudine or a pharmaceutically acceptable derivative thereof in combination with faropenem or a pharmaceutically acceptable derivative or prodrug thereof (e.g. faropenem sodium, faropenem sodium hydrate or faropenem medoxomil), and a pharmaceutically acceptable adjuvant, diluent or carrier.

In a further aspect, the invention relates to a product comprising zidovudine or a pharmaceutically acceptable derivative thereof and an antimicrobial compound selected from nitrofurantoin, mecillinam, fosfomycin, cephalexin and faropenem or a pharmaceutically acceptable derivative or prodrug thereof, as a combined preparation for simultaneous, separate or sequential use in killing multiplying microorganisms associated with a microbial infection. Preferably for killing multiplying bacteria associated with a bacterial infection, e.g. a gram-negative bacterial infection.

BRIEF DESCRIPTION OF THE DRAWINGS

FIG. 1 is a table showing FICI values of zidovudine (AZT) and nitrofurantoin.

FIG. 2 is a table showing FICI values of zidovudine (AZT) and faropenem.

FIG. 3 is a table showing FICI values of t zidovudine (AZT) and mecillinam.

FIG. 4 is a table showing FICI values of zidovudine (AZT) and cephalexin.

FIG. 5 is a table showing FICI values of zidovudine (AZT) and fosfomycin.

DETAILED DESCRIPTION OF THE INVENTION

As used herein, the expressions "combination of" and "in combination with" cover separate, sequential and simultaneous administration of the agents. Unless specified to the contrary, the expressions are also intended to exclude any additional actives, e.g. "a combination of zidovudine and nitrofurantoin" means that zidovudine and nitrofurantoin are administered separately, sequentially or simultaneously but that no other actives are administered.

When the agents are administered sequentially, either the zidovudine or the antimicrobial compound may be administered first. When administration is simultaneous, the agents may be administered either in the same or a different pharmaceutical composition. Adjunctive therapy, i.e. where one agent is used as a primary treatment and the other agent(s) is used to assist that primary treatment, is also an embodiment of the present invention.

The combinations of the present invention may be used to treat microbial infections. In particular they may be used to kill multiplying and/or clinically latent microorganisms associated with microbial infections, preferably multiplying microorganisms associated with microbial infections, e.g. multiplying bacteria associated with Gram-negative bacterial infections. References herein to the treatment of a microbial infection therefore include killing multiplying and/or clinically latent microorganisms associated with such infections.

As used herein, "kill" means a loss of viability as assessed by a lack of metabolic activity.

As used herein, "clinically latent microorganism" means a microorganism that is metabolically active but has a growth rate that is below the threshold of infectious disease expression. The threshold of infectious disease expression refers to the growth rate threshold below which symptoms of infectious disease in a host are absent.

The metabolic activity of clinically latent microorganisms can be determined by several methods known to those skilled in the art; for example, by measuring mRNA levels in the microorganisms or by determining their rate of uridine uptake. In this respect, clinically latent microorganisms, when compared to microorganisms under logarithmic growth conditions (in vitro or in vivo), possess reduced but still significant levels of:

(I) mRNA (e.g. from 0.0001 to 50%, such as from 1 to 30, 5 to 25 or 10 to 20%, of the level of mRNA); and/or (II) uridine (e.g. [$^3$H]uridine) uptake (e.g. from 0.0005 to 50%, such as from 1 to 40, 15 to 35 or 20 to 30% of the level of [$^3$H]uridine uptake).

Clinically latent microorganisms typically possess a number of identifiable characteristics. For example, they may be viable but non-culturable; i.e. they cannot typically be detected by standard culture techniques, but are detectable and quantifiable by techniques such as broth dilution counting, microscopy, or molecular techniques such as polymerase chain reaction. In addition, clinically latent microorganisms are phenotypically tolerant, and as such are sensitive (in log phase) to the biostatic effects of conventional antimicrobial agents (i.e. microorganisms for which the minimum inhibitory concentration (MIC) of a conventional antimicrobial is substantially unchanged); but possess drastically decreased susceptibility to drug-induced killing (e.g. microorganisms for which, with any given conventional antimicrobial agent, the ratio of minimum microbiocidal concentration (e.g. minimum bactericidal concentration, MBC) to MIC is 10 or more).

As used herein, the term "microorganisms" means fungi and bacteria. References herein to "microbial", "antimicrobial" and "antimicrobially" shall be interpreted accordingly. For example, the term "microbial" means fungal or bacterial, and "microbial infection" means any fungal or bacterial infection.

In one embodiment of the invention, one or more of the aforementioned combinations is used to treat a bacterial infection, in particular the combinations may be used to kill multiplying and/or clinically latent microorganisms associated with a bacterial infection. Preferably multiplying bacteria associated with a bacterial infection. As used herein, the term "bacteria" (and derivatives thereof, such as "microbial infection") includes, but is not limited to, references to organisms (or infections due to organisms) of the following classes and specific types:

Gram-positive cocci, such as Staphylococci (e.g. *Staph. aureus, Staph. epidermidis, Staph. saprophyticus, Staph. auricularis, Staph. capitis capitis, Staph. c. ureolyticus, Staph. caprae, Staph. cohnii cohnii, Staph. c. urealyticus, Staph. equorum, Staph. gallinarum, Staph. haemolyticus, Staph. hominis hominis, Staph. h. novobiosepticius, Staph. hyicus, Staph. intermedius, Staph. lugdunensis, Staph. pasteuri, Staph. saccharolyticus, Staph. schleiferi schleiferi, Staph. s. coagulans, Staph. sciuri, Staph. simulans, Staph. warneri* and *Staph. xylosus*); Streptococci (e.g. beta-haemolytic, pyogenic streptococci (such as *Strept. agalactiae, Strept. canis, Strept dysgalactiae dysgalactiae, Strept dysgalactiae equisimilis, Strept equi equi, Strept equi zooepidemicus, Strept. iniae, Strept porcinus* and *Strept pyogenes*), microaerophilic, pyogenic streptococci (*Streptococcus "milleri"*, such as *Strept. anginosus, Strept constellatus constellatus, Strept constellatus pharyngidis* and *Strept intermedius*), oral streptococci of the "mitis" (alpha-haemolytic—*Streptococcus "viridans"*, such as *Strept. mitis, Strept. oralis, Strept. sanguinis, Strept. cristatus, Strept gordonii* and *Strept. parasanguinis*), "salivarius" (non-haemolytic, such as *Strept salivarius* and *Strept vestibularis*) and "mutans" (tooth-surface streptococci, such as *Strept. criceti, Strept. mutans, Strept ratti* and *Strept sobrinus*) groups, *Strept. acidominimus, Strept. bovis, Strept. faecalis, Strept. equinus, Strept pneumoniae* and *Strept. suis*, or Streptococci alternatively classified as Group A, B, C, D, E, G, L, P, U or V *Streptococcus*);

Gram-negative cocci, such as *Neisseria gonorrhoeae, Neisseria meningitidis, Neisseria cinerea, Neisseria elongata, Neisseria flavescens, Neisseria lactamica, Neisseria mucosa, Neisseria sicca, Neisseria subflava* and *Neisseria weaveri*; Bacillaceae, such as *Bacillus anthracis, Bacillus subtilis, Bacillus thuringiensis, Bacillus stearothermophilus* and *Bacillus cereus*; Enterobacteriaceae, such as *Escherichia coli, Enterobacter* (e.g. *Enterobacter aerogenes, Enterobacter agglomerans* and *Enterobacter cloacae*), *Citrobacter* (such as *Citrob. freundii* and *Citrob. divernis*), *Hafnia* (e.g. *Hafnia Erwinia* (e.g. *Erwinia persicinus*), *Morganella morganii, Salmonella* (*Salmonella enterica* and *Salmonella typhi*), *Shigella* (e.g. *Shigella dysenteriae, Shigella flexneri, Shigella boydii* and *Shigella sonne*), *Klebsiella* (e.g. *Klebs. pneumoniae, Klebs. oxytoca, Klebs. ornitholytica, Klebs. planticola, Klebs. ozaenae, Klebs. terrigena, Klebs. granulomatis* (*Calymmatobacterium granulomatis*) and *Klebs. rhinoscleromatis*), *Proteus* (e.g. *Pr. mirabilis, Pr. rettgeri* and *Pr. vulgaris*), *Providencia* (e.g. *Providencia alcalifaciens, Providencia rettgeri* and *Providencia stuartii*), *Serratia* (e.g. *Serratia marcescens* and *Serratia liquifaciens*), and *Yersinia* (e.g. *Yersinia enterocolitica, Yersinia pestis* and *Yersinia pseudotuberculosis*); Enterococci (e.g. *Enterococcus avium, Enterococcus casseliflavus, Enterococcus cecorum, Enterococcus dispar, Enterococcus durans, Enterococcus faecalis, Enterococcus faecium, Enterococcus flavescens, Enterococcus gallinarum, Enterococcus hirae, Enterococcus malodoratus, Enterococcus mundtii, Enterococcus pseudoavium, Enterococcus raffinosus* and *Enterococcus solitarius*); *Helicobacter* (e.g. *Helicobacter pylori, Helicobacter cinaedi* and *Helicobacter fennelliae*); *Acinetobacter* (e.g. *A. baumanii, A. calcoaceticus, A. haemolyticus, A. johnsonii, A. junii, A. lwoffi* and *A. radioresistens*); *Pseudomonas* (e.g. *Ps. aeruginosa, Ps. maltophilia* (*Stenotrophomonas maltophilia*), *Ps. alcaligenes, Ps. chlororaphis, Ps. fluorescens, Ps. luteola. Ps. mendocina, Ps. monteilii, Ps. oryzihabitans, Ps. pertocinogena, Ps. pseudalcaligenes, Ps. putida* and *Ps. stutzen*); *Bacteroides fragilis*; *Peptococcus* (e.g. *Peptococcus niger*); *Peptostreptococcus*; *Clostridium* (e.g. *C. perfringens, C. difficile, C. botulinum, C. tetani, C. absonum, C. argentinense, C. baratii, C. bifermentans, C. beijerinckii, C. butyricum, C. cadaveris, C. carnis, C. celatum, C. clostridioforme, C. cochlearium, C. cocleatum, C. fallax, C. ghonfi, C. glycolicum, C. haemolyticum, C. hastiforme, C. histolyticum, C. indolis, C. innocuum, C. irregulare, C. leptum, C. limosum, C. malenominatum, C. novyi, C. oroticum, C. paraputrificum, C. piliforme, C. putrefasciens, C. ramosum, C. septicum, C. sordelii, C. sphenoides, C. sporogenes, C. subterminale, C. symbiosum* and *C. tertium*); *Mycoplasma* (e.g. *M. pneumoniae, M. hominis, M. genitalium* and *M. urealyticum*); Mycobacteria (e.g. *Mycobacterium tuberculosis, Mycobacterium avium, Mycobacterium fortuitum, Mycobacterium marinum, Mycobacterium kansasii, Mycobacterium chelonae, Mycobacterium abscessus, Mycobacterium leprae, Mycobacterium smegmitis, Mycobacterium africanum, Mycobacterium alvei, Mycobacterium asiaticum, Mycobacterium aurum, Mycobacterium bohemicum, Mycobacterium bovis, Mycobacterium branderi, Mycobacterium brumae, Mycobacterium celatum,*

*Mycobacterium chubense, Mycobacterium confluentis, Mycobacterium conspicuum, Mycobacterium cook ii, Mycobacterium flavescens, Mycobacterium gadium, Mycobacterium gastri, Mycobacterium genavense, Mycobacterium gordonae, Mycobacterium goodii, Mycobacterium haemophilum, Mycobacterium hassicum, Mycobacterium intracellulare, Mycobacterium interjectum, Mycobacterium heidelberense, Mycobacterium lentiflavum, Mycobacterium malmoense, Mycobacterium microgenicum, Mycobacterium microti, Mycobacterium mucogenicum, Mycobacterium neoaurum, Mycobacterium nonchromogenicum, Mycobacterium peregrinum, Mycobacterium phlei, Mycobacterium scrofulaceum, Mycobacterium shimoidei, Mycobacterium simiae, Mycobacterium szulgai, Mycobacterium terrae, Mycobacterium thermoresistabile, Mycobacterium triplex, Mycobacterium triviale, Mycobacterium tusciae, Mycobacterium ulcerans, Mycobacterium vaccae, Mycobacterium wolinskyi* and *Mycobacterium xenopi*); *Haemophilus* (e.g. *Haemophilus influenzae, Haemophilus ducreyi, Haemophilus aegyptius, Haemophilus parainfluenzae, Haemophilus haemolyticus* and *Haemophilus parahaemolyticus*); *Actinobacillus* (e.g. *Actinobacillus actinomycetemcomitans, Actinobacillus equuli, Actinobacillus hominis, Actinobacillus lignieresii, Actinobacillus suis* and *Actinobacillus ureae*); *Actinomyces* (e.g. *Actinomyces israelii*); *Brucella* (e.g. *Brucella abortus, Brucella canis, Brucella melintensis* and *Brucella suis*); *Campylobacter* (e.g. *Campylobacter jejuni, Campylobacter coli, Campylobacter lari* and *Campylobacter fetus*); *Listeria monocytogenes*; *Vibrio* (e.g. *Vibrio cholerae* and *Vibrio parahaemolyticus, Vibrio alginolyticus, Vibrio carchariae, Vibrio fluvialis, Vibrio furnissii, Vibrio hollisae, Vibrio metschnikovii, Vibrio mimicus* and *Vibrio vulnificus*); *Erysipelothrix rhusopathiae*; Corynebacteriaceae (e.g. *Corynebacterium diphtheriae, Corynebacterium jeikeum* and *Corynebacterium urealyticum*); Spirochaetaceae, such as *Borrelia* (e.g. *Borrelia recurrentis, Borrelia burgdorferi, Borrelia afzelii, Borrelia andersonii, Borrelia bissettii, Borrelia garinii, Borrelia japonica, Borrelia lusitaniae, Borrelia tanukii, Borrelia turdi, Borrelia valaisiana, Borrelia caucasica, Borrelia crocidurae, Borrelia duttoni, Borrelia graingeri, Borrelia hermsii, Borrelia hispanica, Borrelia latyschewii, Borrelia mazzottii, Borrelia parkeri, Borrelia persica, Borrelia turicatae* and *Borrelia venezuelensis*) and *Treponema* (*Treponema pallidum* ssp. *pallidum, Treponema pallidum* ssp. *endemicum, Treponema pallidum* ssp. *pertenue* and *Treponema carateum*); *Pasteurella* (e.g. *Pasteurella aerogenes, Pasteurella bettyae, Pasteurella canis, Pasteurella dagmatis, Pasteurella gallinarum, Pasteurella haemolytica, Pasteurella multocida multocida, Pasteurella multocida gallicida, Pasteurella multocida septica, Pasteurella pneumotropica* and *Pasteurella stomatis*); *Bordetella* (e.g. *Bordetella bronchiseptica, Bordetella hinzii, Bordetella holmseii, Bordetella parapertussis, Bordetella pertussis* and *Bordetella trematum*); Nocardiaceae, such as *Nocardia* (e.g. *Nocardia asteroides* and *Nocardia brasiliensis*); *Rickettsia* (e.g. *Ricksettsii* or *Coxiella burneth*); *Legionella* (e.g. *Legionalla anisa, Legionalla birminghamensis, Legionalla bozemanfi, Legionalla cincinnatiensis, Legionalla dumoffii, Legionalla feelefi, Legionalla gormanii, Legionalla hackeliae, Legionalla israelensis, Legionalla jordanis, Legionalla lansingensis, Legionalla longbeachae, Legionalla maceachemii, Legionalla micdadei, Legionalla oakridgensis, Legionalla pneumophila, Legionalla sainthelensi, Legionalla tucsonensis* and *Legionalla wadsworthit*); *Moraxella catarrhalis*; *Cyclospora cayetanensis*; *Entamoeba histolytica*; *Giardia lamblia*; *Trichomonas vaginalis*; *Toxoplasma gondii*; *Stenotrophomonas maltophilia*; *Burkholderia cepacia*; *Burkholderia mallei* and *Burkholderia pseudomallei*; *Francisella tularensis*; *Gardnerella* (e.g. *Gardneralla vaginalis* and *Gardneralla mobiluncus*); *Streptobacillus moniliformis*; Flavobacteriaceae, such as *Capnocytophaga* (e.g. *Capnocytophaga canimorsus, Capnocytophaga cynodegmi, Capnocytophaga gingivalis, Capnocytophaga granulosa, Capnocytophaga haemolytica, Capnocytophaga ochracea* and *Capnocytophaga sputigena*); *Bartonella* (*Bartonella bacilliformis, Bartonella clarridgeiae, Bartonella elizabethae, Bartonella henselae, Bartonella quintana* and *Bartonella vinsonii arupensis*); *Leptospira* (e.g. *Leptospira biflexa, Leptospira borgpetersenii, Leptospira inadai, Leptospira interrogans, Leptospira kirschneri, Leptospira noguchii, Leptospira santarosai* and *Leptospira weilii*); *Spirillium* (e.g. *Spirillum minus*); *Baceteroides* (e.g. *Bacteroides caccae, Bacteroides capillosus, Bacteroides coagulans, Bacteroides distasonis, Bacteroides eggerthii, Bacteroides forsythus, Bacteroides fragilis, Bacteroides merdae, Bacteroides ovatus, Bacteroides putredinis, Bacteroides pyogenes, Bacteroides splanchinicus, Bacteroides stercoris, Bacteroides tectus, Bacteroides thetaiotaomicron, Bacteroides uniformis, Bacteroides ureolyticus* and *Bacteroides vulgatus*); *Prevotella* (e.g. *Prevotella bivia, Prevotella buccae, Prevotella corporis, Prevotella dentalis (Mitsuokella dentalis), Prevotella denticola, Prevotella disiens, Prevotella enoeca, Prevotella heparinolytica, Prevotella intermedia, Prevotella loeschii, Prevotella melaninogenica, Prevotella nigrescens, Prevotella oralis, Prevotella oris, Prevotella oulora, Prevotella tannerae, Prevotella venoralis* and *Prevotella zoogleoformans*); *Porphyromonas* (e.g. *Porphyromonas asaccharolytica, Porphyromonas cangingivalis, Porphyromonas canoris, Porphyromonas cansulci, Porphyromonas catoniae, Porphyromonas circumdentaria, Porphyromonas crevioricanis, Porphyromonas endodontalis, Porphyromonas gingivalis, Porphyromonas gingivicanis, Porphyromonas levii* and *Porphyromonas macacae*); *Fusobacterium* (e.g. *F. gonadiaformans, F. mortiferum, F. naviforme, F. necrogenes, F. necrophorum necrophorum, F. necrophorum fundiliforme, F. nucleatum nucleatum, F. nucleatum fusiforme, F. nucleatum polymorphum, F. nucleatum vincentii, F. periodonticum, F. russii, F. ulcerans* and *F. varium*); *Chlamydia* (e.g. *Chlamydia trachomatis*); *Cryptosporidium* (e.g. *C. parvum, C. hominis, C. canis, C. felis, C. meleagridis* and *C. muris*); *Chlamydophila* (e.g. *Chlamydophila abortus* (*Chlamydia psittaci*), *Chlamydophila pneumoniae* (*Chlamydia pneumoniae*) and *Chlamydophila psittaci* (*Chlamydia psittaci*)); *Leuconostoc* (e.g. *Leuconostoc citreum, Leuconostoc cremoris, Leuconostoc dextranicum, Leuconostoc lactis, Leuconostoc mesenteroides* and *Leuconostoc pseudomesenteroides*); *Gemella* (e.g. *Gemella bergeri, Gemella haemolysans, Gemella morbillorum* and *Gemella sanguinis*); and *Ureaplasma* (e.g. *Ureaplasma parvum* and *Ureaplasma urealyticum*).

Preferably, the bacterial infections treated by the combinations described herein are Gram-negative bacterial infections. Particular Gram-negative bacteria that may be treated using a combination of the invention include:

Enterobacteriaceae, such as *Escherichia coli*, *Klebsiella* (e.g. *Klebs. pneumoniae* and *Klebs. oxytoca*) and *Proteus* (e.g. *Pr. mirabilis*, *Pr. rettgeri* and *Pr. vulgaris*); *Haemophilis influenzae*; Mycobacteria, such as *Mycobacterium tuberculosis*; and *Enterobacter* (e.g. *Enterobacter cloacae*). Preferably, the bacteria are Enterobacteriaceae, such as *Escherichia coli* and *Klebsiella* (e.g. *Klebs. pneumoniae* and *Klebs. oxytoca*). Particularly preferred are *Escherichia coli*, and *Klebs. pneumoniae* (e.g. *Klebs. pneumoniae* subsp. *pneumoniae*).

In all embodiments it is preferable that the combination therapy is synergistic as compared to the administration of the combination components taken alone.

The combination of the present invention is particularly beneficial in treating (multi)-drug-resistant ((M)DR) bacteria. With respect to Enterobacteriaceae, drug resistance most often builds up to carbapenemase i.e. carbapenemase-resistant strains and "extended spectrum β-lactamase" (ESBL) strains for example New Delhi Metallo-beta-lactamase-1 (NDM-1) resistant *Klebs. Pneumonia*, and NDM-1 *E. coli*.

It should be kept in mind that although a combination such as that claimed may initially be demonstrated to be functional in treating (M)DR strains, they can then be used in treating non-resistant strains. This is especially valuable in the context of the presently claimed combination where the primary therapy for Enterobacteriaceae, such as *Escherichia coli*, and *Klebsiella* (e.g. *Klebs. pneumoniae* and *Klebs. oxytoca*) are antimicrobial drugs that are expensive due to prevailing patent protection. The replacement of such "ethical" drugs by a combination of "generic" antibiotics is thought to be beneficial from a therapeutic perspective as well as financial/economic perspective in times where governments are seeking to reduce the cost of healthcare.

The combinations of the present invention may be used to treat infections associated with any of the above-mentioned bacterial organisms, and in particular they may be used for killing multiplying and/or clinically latent microorganisms associated with such an infection, e.g. a Gram-negative bacterial infection.

Particular conditions which may be treated using the combination of the present invention include those which are caused by Gram-negative bacteria such as abscesses, asthma, bacilliary dysentry, bacterial conjunctivitis, bacterial keratitis, bacterial vaginosis, bone and joint infections, bronchitis (acute or chronic), brucellosis, burn wounds, cat scratch fever, cellulitis, chancroid, cholangitis, cholecystitis, cystic fibrosis, cystitis, nephritis, diffuse panbronchiolitis, dental caries, diseases of the upper respiratory tract, empymea, endocarditis, endometritis, enteric fever, enteritis, epididymitis, epiglottitis, eye infections, furuncles, *gardnerella* vaginitis, gastrointestinal infections (gastroenteritis), genital infections, gingivitis, gonorrhoea, granuloma inguinale, Haverhill fever, infected burns, infections following dental operations, infections in the oral region, infections associated with prostheses, intraabdominal abscesses, Legionnaire's disease, leptospirosis, listeriosis, liver abscesses, Lyme disease, lymphogranuloma venerium, mastitis, mastoiditis, meningitis and infections of the nervous system, non-specific urethritis, opthalmia (e.g. opthalmia neonatorum), osteomyelitis, otitis (e.g. otitis externa and otitis media), orchitis, pancreatitis, paronychia, pelveoperitonitis, peritonitis, peritonitis with appendicitis, pharyngitis, pleural effusion, *pneumonia*, postoperative wound infections, postoperative gas gangrene, prostatitis, pseudo-membranous colitis, psittacosis, pyelonephritis, Q fever, rat-bite fever, Ritter's disease, *salmonellosis*, salpingitis, septic arthritis, septic infections, septicameia, systemic infections, tonsillitis, trachoma, typhoid, urethritis, urinary tract infections, wound infections; or infections with, *Escherichia coli*, *Klebs. pneumoniae*, *Klebs. oxytoca*, *Pr. mirabilis*, *Pr. rettgeri*, *Pr. vulgaris*, *Haemophilis influenzae*, *Enterococcus faecalis*, *Enterococcus faecium*, and *Enterobacter cloacae*. In one embodiment the combinations of the invention are used to treat urinary tract infections.

It will be appreciated that references herein to "treatment" extend to prophylaxis as well as the treatment of established diseases or symptoms.

As used herein the term "pharmaceutically acceptable derivative" means: (a) pharmaceutically acceptable salts; and/or (b) solvates (including hydrates).

Pharmaceutically acceptable salts of the compounds included in the combinations of the invention include suitable acid addition or base salts thereof. A review of suitable pharmaceutical salts may be found in Berge et al, J Pharm Sci, 66, 1-19 (1977). Suitable acid addition salts include carboxylate salts (e.g. formate, acetate, trifluoroacetate, propionate, isobutyrate, heptanoate, decanoate, caprate, caprylate, stearate, acrylate, caproate, propiolate, ascorbate, citrate, glucuronate, glutamate, glycolate, α-hydroxybutyrate, lactate, tartrate, phenylacetate, mandelate, phenylpropionate, phenylbutyrate, benzoate, chlorobenzoate, methylbenzoate, hydroxybenzoate, methoxybenzoate, dinitrobenzoate, o-acetoxybenzoate, salicylate, nicotinate, isonicotinate, cinnamate, oxalate, malonate, succinate, suberate, sebacate, fumarate, malate, maleate, hydroxymaleate, hippurate, phthalate or terephthalate salts), halide salts (e.g. chloride, bromide or iodide salts), sulfonate salts (e.g. benzenesulfonate, methyl-, bromo- or chloro-benzenesulfonate, xylenesulfonate, methanesulfonate, ethanesulfonate, propanesulfonate, hydroxyethanesulfonate, 1- or 2-naphthalene-sulfonate or 1,5-naphthalenedisulfonate salts) or sulfate, pyrosulfate, bisulfate, sulfite, bisulfite, phosphate, monohydrogenphosphate, dihydrogenphosphate, metaphosphate, pyrophosphate or nitrate salts. Suitable base salts include metal salts, e.g. sodium, calcium, and amine salts, e.g. e.g. fosfomycin tromethamine.

As used herein the term "prodrug" means the antimicrobial compound, wherein one or more groups have been modified such that the modification may be reversed upon administration to a human or mammalian subject. Such reversion is usually performed by an enzyme naturally present in such subject, though it is possible for a second agent to be administered together with such a prodrug in order to perform the reversion in vivo. Examples of such modifications include ester formation (for example, any of those described above), wherein the reversion may be carried out be an esterase etc. Other such systems will be well known to those skilled in the art.

Mecillinam is for instance known to have an orally active prodrug pivmecillinam. Pivmecillinam, otherwise known as amdinocillin pivoxil, is the pivaloyloxymethyl ester of mecillinam and is used primarily in the treatment of lower urinary tract infections. It is commercially available as the compound per se and in its hydrochloride salt form, and is sold as a generic medication and under the trade name Selixid®.

Pivmecillinam has the following chemical structure:

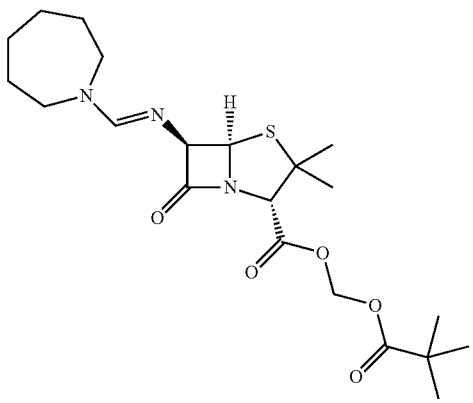 [SMILES: CC(C)(C)C(=O)OCOC(=O)[C@@H]1N2C(=O)[C@@H](/N=C/N3CCCCCC3)[C@H]2SC1(C)C]

Faropenem is also known in the art to have an orally active prodrug: faropenem medoxomil. Faropenem medoxomil is otherwise known as faropenem daloxate and has the structure:

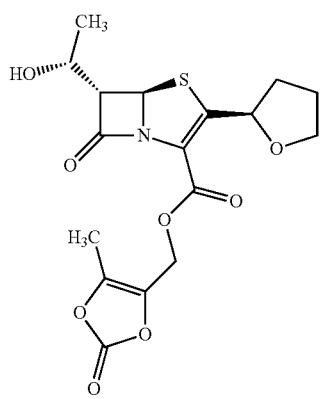 [SMILES: Cc1oc(=O)oc1COC(=O)C1=C([C@H]2CCCO2)S[C@@H]2[C@@H]([C@@H](C)O)C(=O)N12]

The invention includes the use of these known prodrugs of mecillinam and faropenem as well as other prodrugs known in the art for the antimicrobial compounds.

The invention also includes where appropriate all enantiomers and tautomers of the compounds. The skilled person will recognise compounds that possess optical properties (one or more chiral carbon atoms) or tautomeric characteristics. The corresponding enantiomers and/or tautomers may be isolated/prepared by methods known in the art.

Some of the compounds included in the combinations of the invention may exist as stereoisomers and/or geometric isomers—e.g. they may possess one or more asymmetric and/or geometric centres and so may exist in two or more stereoisomeric and/or geometric forms. The present invention contemplates the use of all the individual stereoisomers and geometric isomers of those inhibitor agents, and mixtures thereof. The terms used in the claims encompass these forms, provided said forms retain the appropriate functional activity (though not necessarily to the same degree).

The present invention also includes all suitable isotopic variations of the compounds or pharmaceutically acceptable salts thereof. An isotopic variation or a pharmaceutically acceptable salt thereof is defined as one in which at least one atom is replaced by an atom having the same atomic number but an atomic mass different from the atomic mass usually found in nature. Examples of isotopes that can be incorporated include isotopes of hydrogen, carbon, nitrogen, oxygen, phosphorus, sulphur, fluorine and chlorine such as 2H, 3H, 13C, 14C, 15N, 17O, 18O, 31P, 32P, 35S, 18F and 36Cl, respectively. Certain isotopic variations, for example, those in which a radioactive isotope such as 3H or 14C is incorporated, are useful in drug and/or substrate tissue distribution studies. Tritiated, i.e., 3H, and carbon-14, i.e., 14C, isotopes are particularly preferred for their ease of preparation and detectability. Further, substitution with isotopes such as deuterium, i.e., 2H, may afford certain therapeutic advantages resulting from greater metabolic stability, for example, increased in vivo half-life or reduced dosage requirements and hence may be preferred in some circumstances. Isotopic variations can generally be prepared by conventional procedures using appropriate isotopic variations of suitable reagents.

The compounds for use in the combination of the present invention, including the pharmaceutically acceptable derivatives or prodrugs thereof, are commercially available and/or can be prepared by synthesis methods known in the art. Zidovudine, nitrofurantoin, mecillinam, pivmecillinam, pivmecillinam hydrochloride, fosfomycin, fosfomycin sodium, fosfomycin calcium, fosfomycin trometamol, fosfomycin tromethamine, cephalexin, cephalexin hydrate, cephalexin monohydrate and faropenem sodium hydrate are for example available from Sigma-Aldrich®. Faropenem medoxomil is available from various sources including MuseChem (www.musechem.com).

Zidovudine is 1-[(2R, 4S, 5S)-4-Azido-5-(hydroxymethyl)oxolan-2-yl]-5-methylpyrimidine-2,4-dione, and is available by prescription under the trade name Retrovir®. It is also known as 3'-azido-3'-deoxythymidine or "AZT" and has the following chemical structure:

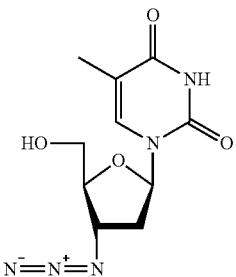

Nitrofurantoin is an oral antibiotic used to treat bladder infections. It is also known as 1-[[[5-nitro-2-furanyl]methylene]amino]-2,4-imidazolidinedione, N-(5-nitro-2-furfurylidene)-1-aminohydantoin, furadoxyl or nitrofurantoine. As well as being commercially available, nitrofurantoin is sold as a generic medication and under various trade names including Macrobid®, Macrodantin®, and Furadantin®. Macrobid® is a hard gelatin capsule shell containing nitrofurantoin in the form of monocrystals and the monohydrate, Macrodantin® is nitrofurantoin macrocrystals in tablet form and Furadantin® is an oral suspension of the compound. As a generic medication nitrofurantoin is available as tablets, capsules and an oral suspension.

Nitrofurantoin has the following chemical structure:

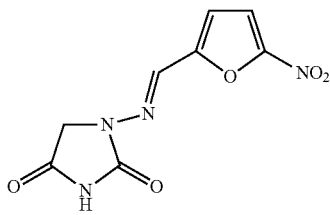 [SMILES: O=C1CN(/N=C/c2ccc([N+](=O)[O-])o2)C(=O)N1]

Mecillinam, otherwise known as amdinocillin, is an extended-spectrum penicillin antibiotic. It is used primarily in the treatment of UTIs and has the following chemical structure:

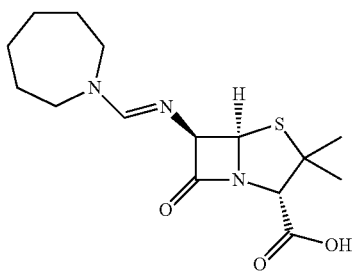 [SMILES: CC1(C)S[C@@H]2[C@H](/N=C/N3CCCCCC3)C(=O)N2[C@H]1C(=O)O]

As well as being commercially available, mecillinam is sold under various trade names including Coactin, Leo, Selexid and Selexidin.

Fosfomycin, also known as phosphomycin or phosphonomycin, is a broad-spectrum antibiotic which is indicated in the treatment of urinary tract infections. It has the chemical name (−)-(1R,2S)-(1,2-epoxypropyl)phosphonic acid and the chemical structure:

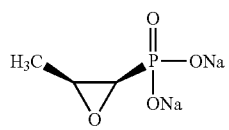

As well as being commercially available in its sodium salt form, calcium salt form, trometamol and tromethamine form, fosfomycin is sold under various trade names including Monourol® and Monuril®. It is also available as a generic medication.

Cephalexin, also spelt cefalexin, is an antibiotic that can treat a number of bacterial infections. It is a beta-lactam antibiotic within the class of first-generation cephalosporins, has the chemical name 7-(D-α-amino-phenylacetamido)-3-methyl-3-cepheme-4-carboxylic acid and the chemical structure:

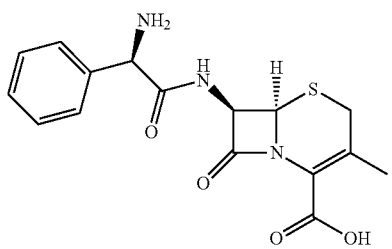 [SMILES: CC1=C(C(=O)O)N2C(=O)[C@@H](NC(=O)[C@H](N)c3ccccc3)[C@H]2SC1]

Cephalexin is commercially available in various salt and hydrate forms. It is sold as a generic medication and under various trade names including Keflex®, Cepol® and Ceporex®.

Faropenem is an orally active beta-lactam antibiotic belonging to the penem group which has the following chemical structure:

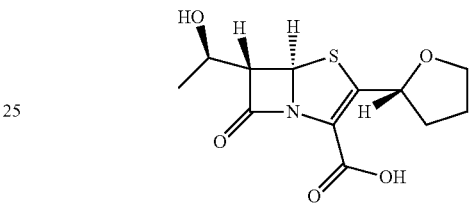

Faropenem is marketed as its sodium salt, faropenem sodium, under the trade name Farom in Japan and Faronem in India. It is also found in its prodrug form, faropenem medoxomil (also known as faropenem daloxate). It is commercially available from Sigma Aldrich® as faropenem sodium hydrate which is also known as (5R,6S,8R,2'R)-2-(2'-tetrahydrofuryl)-6-hydroxyethylpenem-3-carboxylate sodium salt.

Compounds for use according to the invention may be administered as the raw material but are preferably provided in the form of pharmaceutical compositions.

The compounds may be used either as separate formulations or as a single combined formulation. When combined in the same formulation it will be appreciated that the two compounds must be stable and compatible with each other and the other components of the formulation.

Formulations of the invention include those suitable for oral, parenteral (including subcutaneous e.g. by injection or by depot tablet, intrathecal, intramuscular e.g. by depot and intravenous), and rectal or in a form suitable for administration by inhalation or insufflation administration. The most suitable route of administration may depend upon the condition and disorder of the patient. Preferably, the compositions of the invention are formulated for oral administration.

The formulations may conveniently be presented in unit dosage form and may be prepared by any of the methods well known in the art of pharmacy e.g. as described in "Remington: The Science and Practice of Pharmacy", Lippincott Williams and Wilkins, 21$^{st}$ Edition, (2005). Suitable methods include the step of bringing into association to active ingredients with a carrier which constitutes one or more excipients. In general, formulations are prepared by uniformly and intimately bringing into association the active ingredients with liquid carriers or finely divided solid carriers or both and then, if necessary, shaping the product into the desired formulation. It will be appreciated that when the two active ingredients are administered independently, each may be administered by a different means.

When formulated with excipients, the active ingredients may be present in a concentration from 0.1 to 99.5% (such as from 0.5 to 95%) by weight of the total mixture; conveniently from 30 to 95% for tablets and capsules and 0.01 to 50% (such as from 3 to 50%) for liquid preparations.

Formulations suitable for oral administration may be presented as discrete units such as capsules, cachets or tablets (e.g. chewable tablets in particular for paediatric administration), each containing a predetermined amount of active ingredient; as powder or granules; as a solution or suspension in an aqueous liquid or non-aqueous liquid; or as an oil-in-water liquid emulsion or water-in-oil liquid emulsion. The active ingredients may also be presented a bolus, electuary or paste.

A tablet may be made by compression or molding, optionally with one or more excipients. Compressed tablets may be prepared by compressing in a suitable machine the active ingredient in a free-flowing form such as a powder or granules, optionally mixed with other conventional excipients such as binding agents (e.g. syrup, acacia, gelatin, sorbitol, tragacanth, mucilage of starch, polyvinylpyrrolidone and/or hydroxymethyl cellulose), fillers (e.g. lactose, sugar, microcrystalline cellulose, maize-starch, calcium phosphate and/or sorbitol), lubricants (e.g. magnesium stearate, stearic acid, talc, polyethylene glycol and/or silica), disintegrants (e.g. potato starch, croscarmellose sodium and/or sodium starch glycolate) and wetting agents (e.g. sodium lauryl sulphate). Molded tablets may be made by molding in a suitable machine a mixture of the powdered active ingredient with an inert liquid diluent. The tablets may be optionally coated or scored and may be formulated so as to provide controlled release (e.g. delayed, sustained, or pulsed release, or a combination of immediate release and controlled release) of the active ingredients.

Alternatively, the active ingredients may be incorporated into oral liquid preparations such as aqueous or oily suspensions, solutions, emulsions, syrups or elixirs. Formulations containing the active ingredients may also be presented as a dry product for constitution with water or another suitable vehicle before use.

Such liquid preparations may contain conventional additives such as suspending agents (e.g. sorbitol syrup, methyl cellulose, glucose/sugar syrup, gelatin, hydroxymethyl cellulose, carboxymethyl cellulose, aluminium stearate gel and/or hydrogenated edible fats), emulsifying agents (e.g. lecithin, sorbitan mono-oleate and/or acacia), non-aqueous vehicles (e.g. edible oils, such as almond oil, fractionated coconut oil, oily esters, propylene glycol and/or ethyl alcohol), and preservatives (e.g. methyl or propyl p-hydroxybenzoates and/or sorbic acid).

Combinations for use according to the invention may be presented in a pack or dispenser device which may contain one or more unit dosage forms containing the active ingredients. The pack may, e.g. comprise metal or plastic foil, such as a blister pack. Where the compositions are intended for administration as two separate compositions these may be presented in the form of a twin pack.

Pharmaceutical compositions may also be prescribed to the patient in "patient packs" containing the whole course of treatment in a single package, usually a blister pack.

Patient packs have an advantage over traditional prescriptions, where a pharmacist divides a patients' supply of a pharmaceutical from a bulk supply, in that the patient always has access to the package insert contained in the patient pack, normally missing in traditional prescriptions. The inclusion of the package insert has been shown to improve patient compliance with the physician's instructions.

The administration of the combination of the invention by means of a single patient pack, or patients packs of each composition, including a package insert directing the patient to the correct use of the invention is a desirable feature of this invention.

According to a further embodiment of the present invention there is provided a patient pack comprising at least one active of the combination according to the invention and an information insert containing directions on the use of the combination of the invention.

In another embodiment of the invention, there is provided a double pack comprising in association for separate administration, an antimicrobial agent, preferably having biological activity against clinically latent microorganisms, and one or more of the compounds disclosed herein preferably having biological activity against clinically latent microorganisms.

The amount of active ingredients required for use in treatment will vary with the nature of the condition being treated and the age and condition of the patient, and will ultimately be at the discretion of the attendant physician. In general however, doses employed for adult human treatment will typically be in the range of 0.02 to 5000 mg per day, preferably 1 to 1500 mg per day. The desired dose may conveniently be presented in a single dose or as divided doses administered at appropriate intervals, e.g. as two, three, four or more sub-doses per day.

Suitable dosages and formulations for the administration of zidovudine are described in the product label for Retrovir® oral solution or capsules which can be found at http://www.medicines.org.uk/emc/medicine/12444/SPC/Retrovir+250 mg+Capsules/.

Suitable dosages and formulations for the administration of nitrofurantoin are described in the product labels for furadantin oral suspension, macrobid capsules, nitrofurantoin tablets, nitrofurantoin capsules and nitrofurantoin oral suspension. These product labels can be found, for example at:

https://www.medicines.org.uk/emc/product/5749/smpc;
https://www.medicines.org.uk/emc/product/429/smpc;
https://www.medicines.org.uk/emc/product/3602/smpc;
https://www.medicines.org.uk/emc/product/428/smpc;
https://www.medicines.org.uk/emc/product/3601/smpc;
https://www.medicines.org.uk/emc/product/437/smpC;
and https://www.medicines.org.uk/emc/product/7818/smpc.

Suitable dosages and formulations of mecillinam/pivmecillinam are described in the product labels for pivmecillinam tablets and Selexid which can be found at:

https://www.medicines.org.uk/emc/product/4982/smpc;
and
https://www.medicines.org.uk/emc/product/3799/smpc.

Suitable dosages and formulations of fosfomycin are described in the product labels for Fomicyt® powder for solution for infusion, fosfomycin granules for oral solution (containing fosfomycin trometamol) and Monuril® granules for oral solution (containing fosfomycin trometamol). These product labels can be found at:

https://www.medicines.org.uk/emc/product/5439/smpc;
https://www.medicines.org.uk/emc/product/7219/smpc;
and
https://www.medicines.org.uk/emc/product/7329/smpc.

Suitable dosages and formulations of cephalexin are described in the product labels for cephalexin capsules, oral suspension and tablets which can be found at:

https://www.medicines.org.uk/emc/product/3998/smpc;
https://www.medicines.org.uk/emc/product/3990/smpc
https://www.medicines.org.uk/emc/product/5960/smpc;
https://www.medicines.org.uk/emc/product/5960/smpc;
https://www.medicines.org.uk/emc/product/3996/smpc; and
https://www.medicines.org.uk/emc/product/3997/smpc.

Suitable dosages and formulations for faropenem are described in the product label for Farom, the tablet form of faropenem sodium marketed in Japan. This information would be readily obtained and understood by the person skilled in the art.

Biological Tests

Test procedures that may be employed to determine the biological (e.g. bactericidal or antimicrobial) activity of the active ingredients include those known to persons skilled in the art for determining:
 (a) bactericidal activity against clinically latent bacteria; and
 (b) antimicrobial activity against log phase bacteria.

In relation to (a) above, methods for determining activity against clinically latent bacteria include a determination, under conditions known to those skilled in the art (such as those described in *Nature Reviews, Drug Discovery* 1, 895-910 (2002), the disclosures of which are hereby incorporated by reference), of Minimum Stationary-cidal Concentration ("MSC") or Minimum Dormicidal Concentration ("MDC") for a test compound.

By way of example, WO2000028074 describes a suitable method of screening compounds to determine their ability to kill clinically latent microorganisms. A typical method may include the following steps:
 (1) growing a bacterial culture to stationary phase;
 (2) treating the stationery phase culture with one or more antimicrobial agents at a concentration and or time sufficient to kill growing bacteria, thereby selecting a phenotypically resistant sub-population;
 (3) incubating a sample of the phenotypically resistant subpopulation with one or more test compounds or agents; and
 (4) assessing any antimicrobial effects against the phenotypically resistant subpopulation.

According to this method, the phenotypically resistant sub-population may be seen as representative of clinically latent bacteria which remain metabolically active in vivo and which can result in relapse or onset of disease.

In relation to (b) above, methods for determining activity against log phase bacteria include a determination, under standard conditions (i.e. conditions known to those skilled in the art, such as those described in WO 2005014585, the disclosures of which document are hereby incorporated by reference), of Minimum Inhibitory Concentration ("MIC") or Minimum Bactericidal Concentration ("MBC") for a test compound. Specific examples of such methods are described below.

EXAMPLES

Example 1: In Vitro Synergistic Effect of Zidovudine (AZT) and Nitrofurantoin

The chequerboard method used in Example 1 followed the protocols detailed in Antimicrob Chemo (2013) 68, 374-384. Zidovudine and nitrofurantoin were obtained from commercially available sources. The bacteria used was *E. coli* k12; *E. coli* k12 is a sensitive strain which supposes to be susceptible to all antibiotics against Gram-negative bacteria. This strain was obtained from a commercial source and log phase growth of the bacteria was carried out using methods known in the art.

The effects of the combination of the present invention were examined by calculating the fractional inhibitory concentration index (FICI) of each combination, as follows:

(MIC of drug A, tested in combination)/(MIC of drug A, tested alone)+(MIC of drug B, tested in combination)/(MIC of drug B, tested alone).

The interaction of the combination was defined as showing synergy if the FICI was 0.5, no interaction if the FICI was >0.5 but <4.0 and antagonism if the FICI was >4.0.

The FICI values indicate that zidovudine (AZT) and nitrofurantoin have a synergistic effect when used in combination at various concentrations against log phase *E. coli* k12 (FIG. 1).

Example 2: In Vitro Synergistic Effect of Zidovudine in Combination with Faropenem The method and bacterial strain were identical to Example 1. Zidovudine and faropenem were obtained from commercially available sources. The effects of the combination of the present invention were examined by calculating the MIC for each drug alone and in combination in the same manner as Example 1.

The FICI values indicate that zidovudine (AZT) and faropenem have a synergistic effect when used in combination at various concentrations against log phase *E. coli* k12 (FIG. 2).

Example 3: In Vitro Synergistic Effect of Zidovudine in Combination with Mecillinam The method and bacterial strain were identical to Example 1. Zidovudine and mecillinam were obtained from commercially available sources. The effects of the combination of the present invention were examined by calculating the MIC for each drug alone and in combination in the same manner as Example 1.

The FICI values indicate that zidovudine (AZT) and mecillinam have a synergistic effect when used in combination at various concentrations against log phase *E. coli* k12 (FIG. 3).

Example 4: In Vitro Synergistic Effect of Zidovudine in Combination with Cephalexin The method and bacterial strain were identical to Example 1. Zidovudine and cephalexin were obtained from commercially available sources. The effects of the combination of the present invention were examined by calculating the MIC for each drug alone and in combination in the same manner as Example 1.

The FICI values indicate that zidovudine (AZT) and cephalexin have a synergistic effect when used in combination at various concentrations against log phase *E. coli* k12 (FIG. 4).

Example 5: In Vitro Synergistic Effect of Zidovudine in Combination with Fosfomycin The method and bacterial strain were identical to Example 1. Zidovudine and fosfomycin were obtained from commercially available sources. The effects of the combination of the present invention were examined by calculating the MIC for each drug alone and in combination in the same manner as Example 1.

The FICI values indicate that zidovudine (AZT) and fosfomycin have a synergistic effect when used in combination at various concentrations against log phase *E. coli* k12 (FIG. 5).

The invention claimed is:

1. A composition comprising zidovudine or a pharmaceutically acceptable salt and/or solvate thereof and an antimicrobial compound selected from the group consisting of nitrofurantoin, mecillinam, fosfomycin, cephalexin and faropenem, or a pharmaceutically acceptable salt and/or solvate or prodrug thereof.

2. The composition according to claim 1, wherein the antimicrobial compound is nitrofurantoin or a pharmaceutically acceptable salt and/or solvate or prodrug thereof.

3. The composition according to claim 1, wherein the antimicrobial compound is mecillinam or a pharmaceutically acceptable salt and/or solvate or prodrug thereof.

4. The composition according to claim 3, wherein the prodrug of mecillinam is pivmecillinam or a pharmaceutically acceptable salt and/or solvate thereof.

5. The composition according to claim 1, wherein the antimicrobial compound is fosfomycin or a pharmaceutically acceptable salt and/or solvate or prodrug thereof.

6. The composition according to claim 1, wherein the antimicrobial compound is cephalexin or a pharmaceutically acceptable salt and/or solvate or prodrug thereof.

7. The composition according to claim 1, wherein the antimicrobial compound is faropenem or a pharmaceutically acceptable salt and/or solvate or prodrug thereof.

8. A method of treating a microbial infection, the method comprising the step of administering to a mammal in need thereof, the composition according to claim 1.

9. The method according to claim 8 wherein the method kills multiplying microorganisms associated with a microbial infection.

10. The method according to claim 8, wherein the microbial infection is a bacterial infection and the microorganisms are bacteria.

11. The method according to claim 10, wherein the infection is a gram-negative bacterial infection.

12. The method according to claim 10, wherein the infection is a urinary tract infection.

13. The method according to claim 10, wherein the bacterial infection is caused by *E. coli*.

14. The method according to claim 10, wherein the infection is caused by a drug-resistant strain of the bacteria.

15. A pharmaceutical composition comprising zidovudine or a pharmaceutically acceptable salt and/or solvate thereof in combination with an antimicrobial compound selected from the group consisting of nitrofurantoin, mecillinam, fosfomycin, cephalexin and faropenem or a pharmaceutically acceptable salt and/or solvate or prodrug thereof, and a pharmaceutically acceptable adjuvant, diluent or carrier.

16. A product comprising zidovudine or a pharmaceutically acceptable salt and/or solvate thereof and an antimicrobial compound selected from the group consisting of nitrofurantoin, mecillinam, fosfomycin, cephalexin and faropenem or a pharmaceutically acceptable salt and/or solvate or prodrug thereof.

* * * * *